United States Patent
Liu et al.

(10) Patent No.: US 7,646,851 B2
(45) Date of Patent: Jan. 12, 2010

(54) DEVICE AND METHOD FOR GENERATING X-RAYS HAVING DIFFERENT ENERGY LEVELS AND MATERIAL DISCRIMINATION SYSTEM

(75) Inventors: Yaohong Liu, Beijing (CN); Chuanxiang Tang, Beijing (CN); Zhiqiang Chen, Beijing (CN); Huaibi Chen, Beijing (CN); Jinsheng Liu, Beijing (CN); Jianjun Gao, Beijing (CN)

(73) Assignees: Tsinghua University, Beijing, P.R. (CN); Nuctech Company Limited, Beijing, P.R. (CN)

( * ) Notice: Subject to any disclaimer, the term of this patent is extended or adjusted under 35 U.S.C. 154(b) by 55 days.

(21) Appl. No.: 11/788,994

(22) Filed: Apr. 23, 2007

(65) Prior Publication Data

US 2007/0269013 A1    Nov. 22, 2007

(30) Foreign Application Priority Data

May 19, 2006  (CN)  .................... 2006 1 0011944

(51) Int. Cl.
  *H05G 1/64* (2006.01)
  *H05G 2/00* (2006.01)
(52) U.S. Cl. ..................... 378/98.9; 378/119
(58) Field of Classification Search .............. 378/57, 378/64, 65, 98.9, 119
See application file for complete search history.

(56) References Cited

U.S. PATENT DOCUMENTS 3,806,836 A * 4/1974 Alsmeyer ................ 332/106
5,044,006 A * 8/1991 Cyrulnik .................... 378/145
5,471,516 A * 11/1995 Nunan ......................... 378/65
5,811,943 A * 9/1998 Mishin et al. ............... 315/505
5,933,335 A * 8/1999 Hitchcock et al. .............. 363/25

(Continued)

FOREIGN PATENT DOCUMENTS

WO    WO 00/43760    7/2000

OTHER PUBLICATIONS

J. D. Jackson, Classical Electrodynamics, second edition (New York: John Wiley & Sons, 1975), p. 334-350.*

*Primary Examiner*—Allen C. Ho
(74) *Attorney, Agent, or Firm*—Westman, Champlin & Kelly, P.A.

(57) ABSTRACT

Disclosed is a device and method for generating X-rays having different energy levels as well as a material discrimination system thereof. The method comprises the steps of: generating a first pulse voltage, a second pulse voltage, a third pulse voltage and a fourth pulse voltage, generating a first electron beam having a first beam load and a second electron beam having a second beam load, respectively, based on the first pulse voltage and second pulse voltage, generating a first microwave having a first power and a second microwave having a second power, respectively, based on the third pulse voltage and the fourth pulse voltage, accelerating the first and second electron beams respectively using the first and second microwave to obtain the accelerated first electron beam and the second electron beam, hitting a target with the accelerated first electron beam and the second electron beam to generate a first X-ray and a second X-ray having different energy levels. The X-rays having different energy levels generated by the present invention can be used in the non-destructive inspection for large-sized container cargo at places such as Customs, ports and airports, and in realizing the material discrimination for the inspected object.

11 Claims, 5 Drawing Sheets

U.S. PATENT DOCUMENTS

| | | | |
|---|---|---|---|
| 6,038,284 A * | 3/2000 | Hernandez-Guerra et al. | 378/65 |
| 6,069,936 A | 5/2000 | Bjorkholm | 378/98.9 |
| 6,301,326 B2 * | 10/2001 | Bjorkholm | 378/57 |
| 6,407,505 B1 * | 6/2002 | Bertsche | 315/5.41 |
| 6,493,424 B2 * | 12/2002 | Whitham | 378/137 |
| 6,856,105 B2 * | 2/2005 | Yao et al. | 315/505 |
| 7,130,371 B2 * | 10/2006 | Elyan et al. | 378/57 |
| 7,140,771 B2 * | 11/2006 | Leek | 378/203 |
| 7,162,005 B2 * | 1/2007 | Bjorkholm | 378/57 |
| 7,208,889 B2 * | 4/2007 | Zavadtsev et al. | 315/500 |
| 7,391,849 B2 * | 6/2008 | Smith | 378/109 |
| 2007/0274445 A1 * | 11/2007 | Zavadtsev et al. | 378/57 |

* cited by examiner

DEVICE AND METHOD FOR GENERATING X-RAYS HAVING DIFFERENT ENERGY LEVELS AND MATERIAL DISCRIMINATION SYSTEM

FIELD OF THE INVENTION

The present invention relates to an electron linac (electron linear accelerator) for radiographic imaging of large and medium-sized objects, more particularly, to an electron linear acceleration device for generating X-rays having different energy levels and a method thereof as well as a material discrimination system, which can discriminate the material contained in the large and medium-sized objects such as cargo or air cargo containers.

BACKGROUND OF THE INVENTION

The present application claims priority of Chinese patent application Ser. No. 200610011944.4, filed May 19, 2006, the content of which is hereby incorporated by reference in its entirety.

The existing cargo inspection system based on radiographic imaging generally causes a single energy radiation to interact with the object under inspection, and then detects the radiation having penetrated the object under inspection to obtain an image. Although such a system can reflect the change in shape and mass thickness of the object under inspection, it can't discriminate the material property of the object under inspection.

As the concern on global anti-terrorism grows, the inspection requirements for dangerous and prohibited articles are enhanced, whereby various detection means being proposed, in which a material discrimination method employing dual-energy X-ray imaging can achieve the discrimination between substances' effective atomic numbers, therefore is widely used in low energy range (<450 keV). As is well known, photoelectric absorption and Compton scatter effects predominate when X-rays within low energy range interact with the substance. Since the relationship between attenuation index corresponding to photoelectric absorption effect and atomic number is $\mu_{photo} \propto Z^4$, the dual-energy method is well capable of distinguishing the difference between various atomic numbers.

However, when X-rays within high energy range (>1 MeV) interact with the substance, electron pair generation and Compton scatter effects predominate, and the relationship between attenuation index corresponding to electron pair generation effect and atomic number is $\mu_{pair} \propto Z$, which makes the sensitivity of the dual-energy method low in distinguishing atomic numbers in high energy range. Thus the requirement for the system detection accuracy is very high. The U.S. Pat. No. 6,069,936 and the international application WO 0043760 both disclose that a single high-energy X-ray source is employed, and two X-ray beams having different energy spectra are obtained through the absorption of specific material. However, since a single high-energy X-ray generates only one original energy spectrum, the energy spectra of two radiation beams obtained through the absorption of specific material will become almost the same after the two ray beams having different energy spectra pass through the inspected object of large mass thickness and attenuate accordingly. At this time it is impossible to distinguish the effective atomic number of the substance. If two beams of high-energy X-rays having different original energy levels and spectra are generated respectively by using tow radiation sources in order to identify material, the system will be too complex and costly. Consequently, it has been considering as impractical to implement large-sized object inspection and material discrimination by the dual-energy method in high energy range.

SUMMARY OF THE INVENTION

In view of the above problem with the prior art, the present invention is accomplished. It is an object of the present invention to provide an electron linac for generating X-rays having different energy levels and a method thereof as well as a material discrimination system, which can alternately generate electron beams having different energy spectra, of which the energy levels are distinct from each other, and alternately generate X-rays having different energy spectra by use of electron beam targeting. By causing X-rays of two energy levels to interact with the substance, it is possible to non-destructively inspect large and medium-sized objects and identify the material contained.

According to the first aspect of the present invention, there is provided a device for alternately generating X-rays having different energy levels comprising: a pulse modulation means for generating a first pulse voltage, a second pulse voltage, a third pulse voltage and a fourth pulse voltage; an electron beam generation means for generating a first electron beam having a first beam load and a second electron beam having a second beam load, respectively, based on the first pulse voltage and the second pulse voltage; a microwave generation means for generating a first microwave having a first power and a second microwave having a second power, respectively, based on the third pulse voltage and the fourth pulse voltage; an electron beam acceleration means for accelerating the first electron beam and the second electron beam respectively using the first microwave and the second microwave to obtain the accelerated first electron beam and the accelerated second electron beam; and a target to be hit by the accelerated first electron beam and the accelerated second electron beam to generate a first X-ray and a second X-ray having different energy levels.

According to an embodiment of the present invention, the electron beam generation means comprises a grid-controlled electron gun, and the pulse modulation means comprises a power supply whose grid pulse amplitudes alternate.

According to an embodiment of the present invention, the first beam load is greater than the second beam load, and the first power is smaller than the second power.

According to an embodiment of the present invention, the first beam load is smaller than the second beam load, and the first power is greater than the second power.

According to an embodiment of the present invention, the microwave generation means alternately change the intensity of magnetic field in synchronization with the third pulse voltage and the fourth pulse voltage to generate the first microwave and the second microwave.

According to an embodiment of the present invention, the microwave generation means is a magnetron or a klystron.

According to an embodiment of the present invention, the electron beam acceleration means is a traveling wave acceleration tube or a standing wave acceleration tube.

According to another aspect of the present invention, there is provided a material discrimination system comprising: the device as described above; a synchronization control means for generating a synchronization control signal; a detection means for detecting X-rays after the first X-ray and second X-ray generated by the device interact with the inspected object, based on the synchronization control signal generated by the synchronization control means, to generate digital signals; and an image processing and material discrimination means for classifying the digital signals for the inspected object with a predefined calibration curve to discriminate the material of the inspected object.

According to another aspect of the present invention, there is provided a device for alternately generating X-rays having different energy levels comprising: a pulse modulation means for generating a first pulse voltage and a second pulse voltage; an electron beam generation means for generating a first electron beam having a first beam load and a second electron beam having a second beam load, respectively, based on the first pulse voltage and second pulse voltage; a microwave generation means for changing the intensity of magnetic field in synchronization with the first pulse voltage and second pulse voltage to generate a first microwave having a first power and a second microwave having a second power; an electron beam acceleration means for accelerating the first electron beam and the second electron beam respectively using the first microwave and the second microwave to obtain the accelerated first electron beam and the second electron beam; and a target to be hit by the accelerated first electron beam and accelerated second electron beam to generate a first X-ray and a second X-ray having different energy levels According to still another aspect of the present invention, there is provided a method for alternately generating X-rays having different energy levels comprises the steps of: generating a first pulse voltage, a second pulse voltage, a third pulse voltage and a fourth pulse voltage; generating a first electron beam having a first beam load and a second electron beam having a second beam load, respectively, based on the first pulse voltage and second pulse voltage; generating a first microwave having a first power and a second microwave having a second power, respectively, based on the third pulse voltage and fourth pulse voltage; accelerating the first electron beam and second electron beam respectively using the first microwave and second microwave to obtain the accelerated first electron beam and the second electron beam; and hitting a target with the accelerated first electron beam and accelerated second electron beam to generate a first X-ray and a second X-ray having different energy levels.

As a result, the accelerated electron beams having different energy levels can be obtained by changing synchronously the beam load intensity of the accelerator. Meanwhile, the energy level difference between two accelerated electron beams can be further widened by synchronously changing the microwave power fed into the acceleration tube. The X-rays, which result from the targeting by the two electron beams having different energy levels, have a large difference between energy levels, that is, a great distinction between the energy spectra of the two X-ray beams.

With the present invention, by changing the relevant preset parameters to change the pulse voltages of the electron gun and the microwave power, the electron beams having different energy levels can be obtained and thereby the X-rays having different energy levels. This requires no structural change in the accelerator and can meet the requirements of variety of applications.

In addition, the alternately generated high-energy X-rays with a large energy difference can implement the material discrimination for large and medium-sized objects with a higher accuracy.

Further, the present invention realizes a rapid switching between two different energy levels by circuit configuration, thereby overcoming the limitation of the conventional energy switch with a mechanic structure, that is, the mechanic switch has difficulty in rapid switching between two different energy levels and has a short life.

DETAILED DESCRIPTION OF THE PREFERRED EMBODIMENTS

Hereafter an embodiment of the present invention will be explained in detail with reference to the drawings.

Figure 1A:
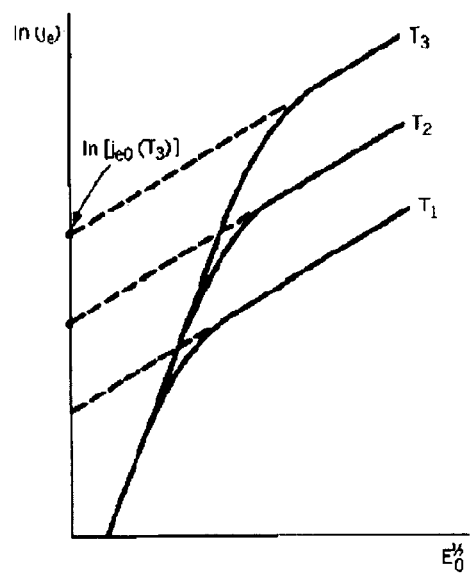
FIG. 1A shows the electron-emitting characteristic of an electron gun.
Figure 1B:
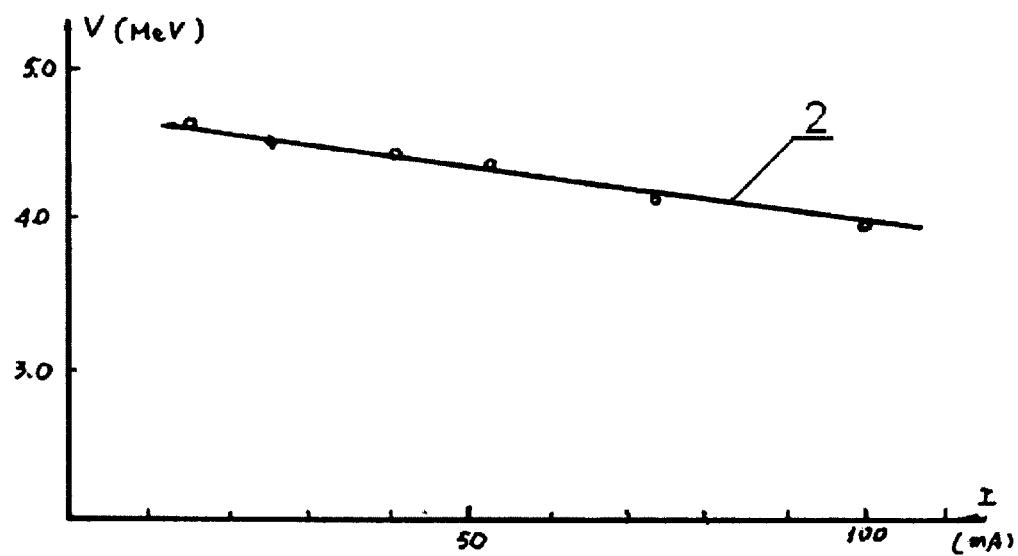
FIG. 1B is a schematic diagram of accelerated electron energy varying with beam load.
Figure 1C:
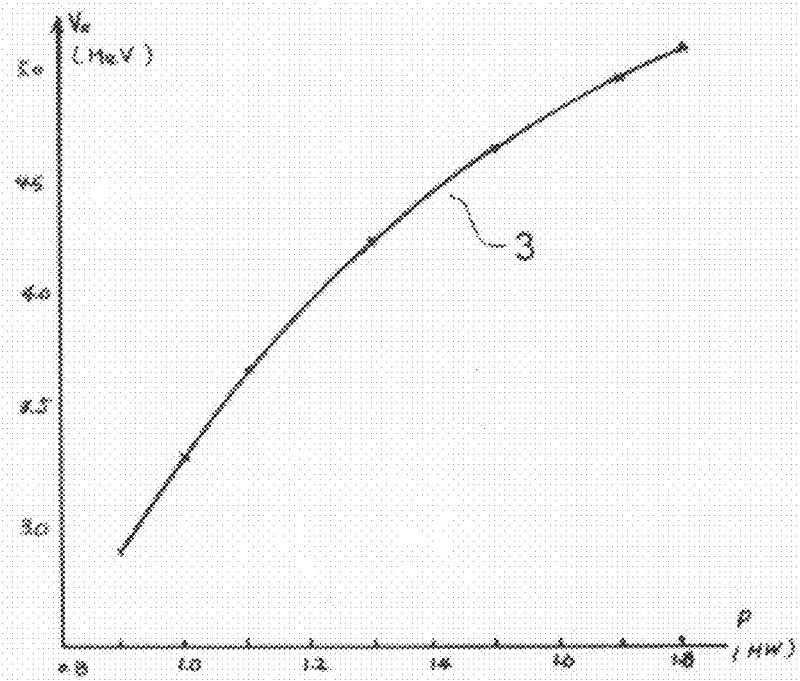
FIG. 1C is a schematic diagram of accelerated electron energy varying with fed microwave power.
Figure 2:
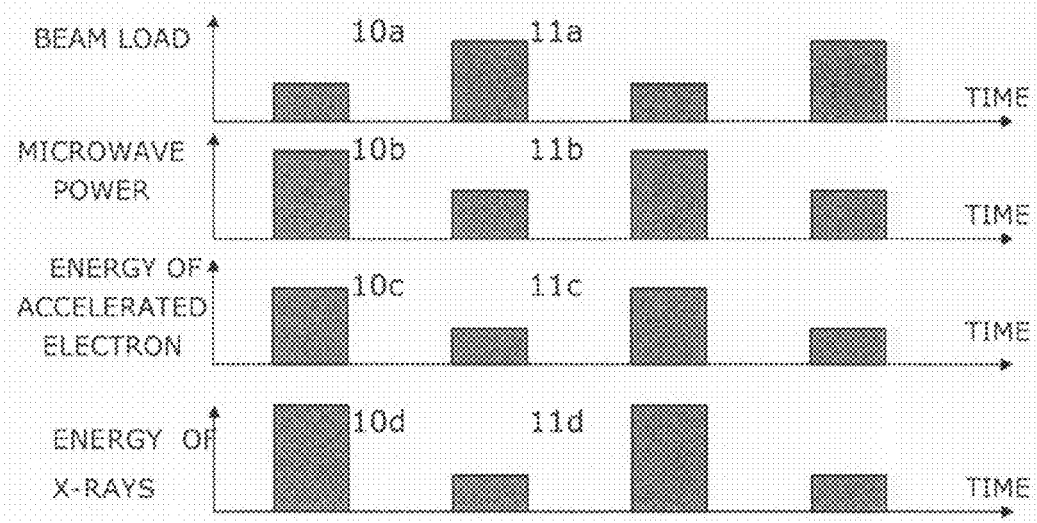
FIG. 2 is a schematic diagram of the parameter relationship between respective main systems of the accelerator while alternately generating X-rays having different energy levels according to an embodiment of the present invention.

FIG. 1A shows the electron-emitting characteristic of an electron gun. FIG. 1B is a schematic diagram of accelerated electron energy varying with beam load. FIG. 1C is a schematic diagram of accelerated electron energy varying with fed microwave power. FIG. 2 is a schematic diagram of the parameter relationship between respective main systems of the accelerator while alternately generating X-rays having different energy levels according to an embodiment of the present invention.

As shown in FIG. 1A, the electron gun has different capabilities of electron emission under different voltage amplitudes. The pulse modulator for driving the electron gun generates high voltages having two different amplitudes, which cause the electron gun to emit electron beams having different current intensities, that is, the obtained electron beams having different beam loads as shown in FIG. 2.

The beam load effect is represented by the formula $E=\sqrt{AP}-BI$, where E is the energy of accelerated electrons, I is the beam intensity of accelerated electrons, P is the microwave power fed into the acceleration section, and A and B are preset constants. According to the beam load effect, different electron beams are accelerated to obtain high-energy electron beams having different energy levels.

FIG. 1B is a schematic diagram showing the beam load effect. As shown in Curve 2 of FIG. 1B, the higher the intensity of the beam load, the less the energy obtained by accelerating the beam in the acceleration tube. When the intensity of the pulse electron beam is high, that is, the intensity of the beam load is great, a small microwave power is fed into the acceleration tube, thereby obtaining a electron beam of a relatively low energy level. On the contrary, when the intensity of the beam load of the electron beam is small, a large microwave power is fed, thereby obtaining an electron beam having a relatively high energy level.

Figure 3:
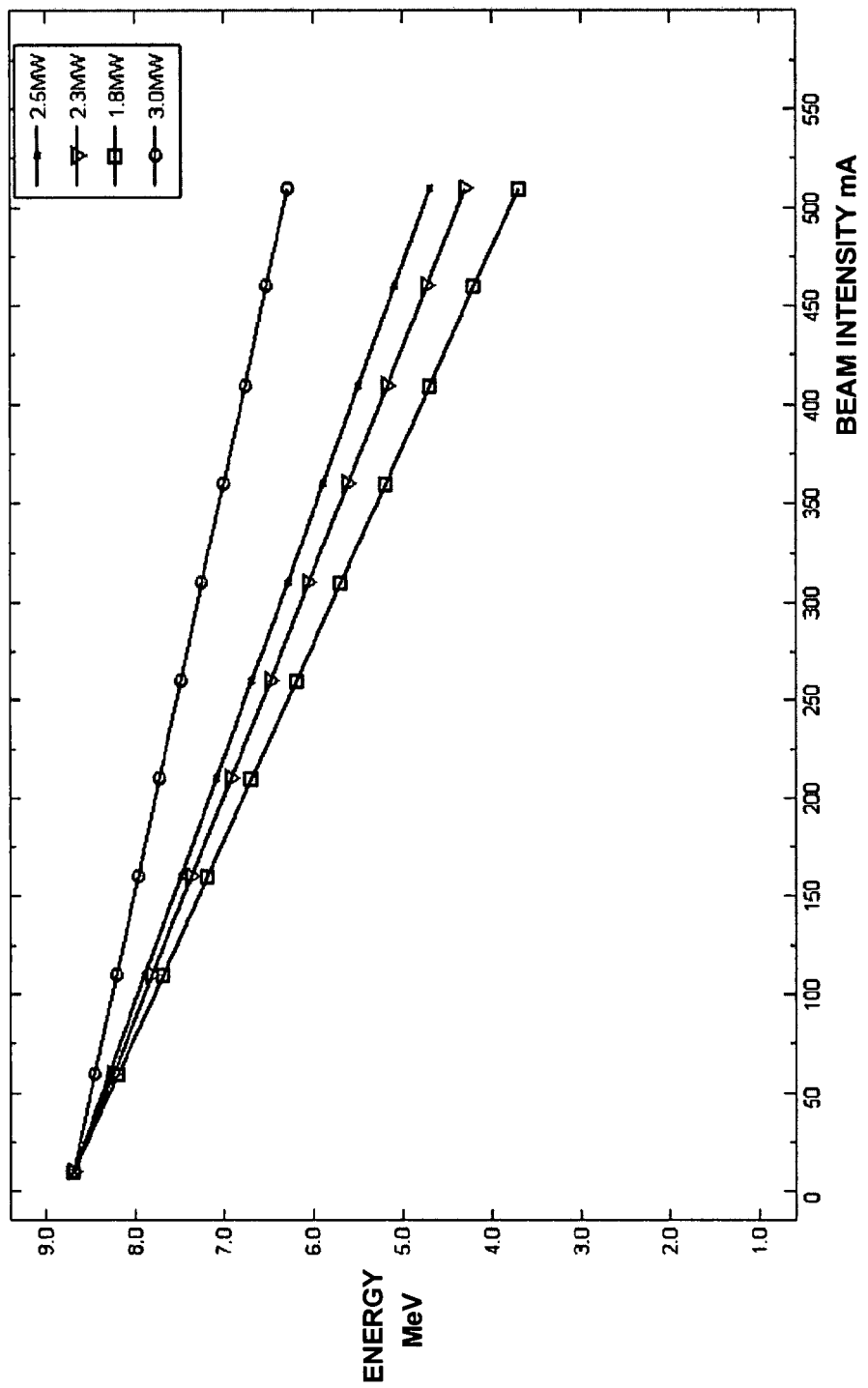
FIG. 3 is a schematic diagram of the variation in accelerated electron energy when simultaneously changing beam load and fed microwave power.

FIG. 3 is a schematic diagram of the energy variation in accelerated electrons when simultaneously changing beam load and fed microwave power. As shown in FIG. 3, if the fed microwave power is changed in synchronization with the change in the beam load, the energy finally obtained by accelerating the electron beams will further vary, thereby resulting in greater energy difference between the accelerated electron beams having two different beam loads.

Thus, if the first and the second electron beams having beam loads 10a and 11a respectively are accelerated under the completely same condition, two electron beams having different energy levels will be obtained. Meanwhile, the microwave power fed into the acceleration tube is changed to produce the first and the second microwaves having microwave powers 10b and 11b respectively. As shown in FIG. 2, the power of the first microwave is greater than that of the second one.

Curve 3 of FIG. 1C shows the characteristic of the beam acceleration by the acceleration tube provided with different microwave powers. As can be seen in FIG. 1C, when the beam load is fixed, the greater the fed microwave power is, the higher the energy obtained by accelerating the beam is. If the system operates in the first mode, i.e. the high-energy mode, the first electron beam having the beam load 10a is accelerated with the first microwave having the microwave power 10b to obtain a high-energy electron beam having the electron beam energy 10c. Then the high-energy electron beam is caused to hit a target to generate a high-energy X-ray with its energy being 10d.

If the system operates in the second mode, i.e. the low-energy mode, the second microwave having the power 11b, whose amplitude is smaller than the power 10b of the first microwave, will be fed into the acceleration tube. The second electron beam having the beam load 11a is accelerated to obtain a low-energy electron beam of the electron beam energy 11c. Then the low-energy electron beam is caused to hit the target to generate a low-energy X-ray with its energy being 11d. In this manner, the system alternately changes between the high-energy mode and the low-energy mode so as to generate X-rays with their energy levels alternately changing.

Figure 4A:
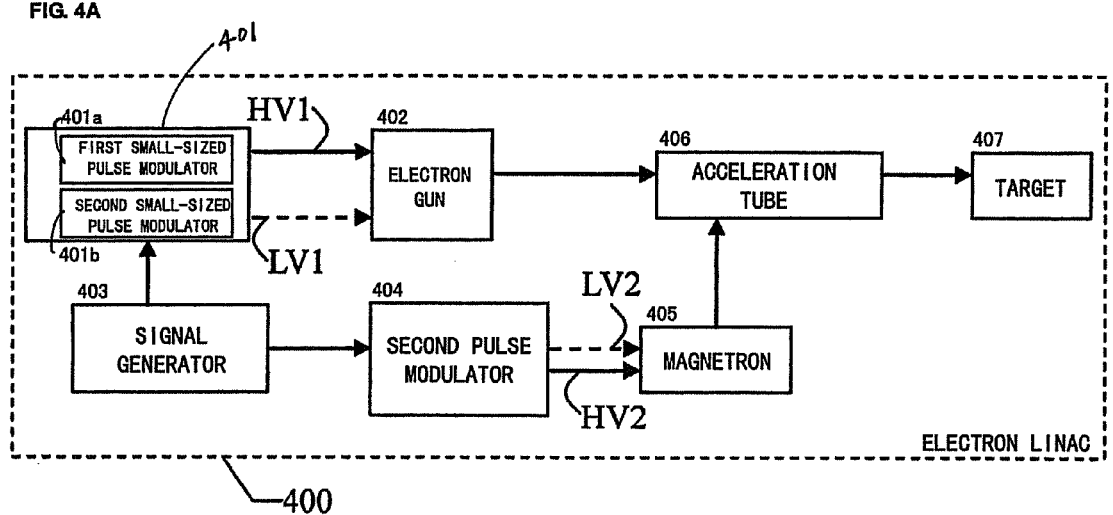
FIG. 4A is a structural schematic diagram of the electron linac according to an embodiment of the present invention.

FIG. 4A is a structural schematic diagram of the electron linac according to an embodiment of the present invention. As shown in FIG. 4A, the electron linac 400 of the embodiment is an electron linac alternately generating dual-energy X-rays. The electron linac 400 includes a signal generator 403, a first and a second pulse modulator 401 and 404 connected to the signal generator 403, an electron gun 402 connected to the first pulse modulator 401, a magnetron 405 connected to the second pulse modulator 404, an acceleration tube 406 connected to the electron gun 402 and the magnetron 405, and a target 407 on which the rays generated by the acceleration tube 406 hit.

The signal generator 403 can generate high-level and low-level signals at a fixed frequency depending on predefined parameters. The first small-sized pulse modulator 401a and the second small-sized pulse modulator 4041b generate high voltages having different amplitudes, for example, a first high voltage having the first amplitude and a second high voltage having the second amplitude, based on the signals generated by the signal generator 403. Depending on different systems, the functions of the first small-sized pulse modulator 401a and the second small-sized pulse modulator 4041b can be fulfilled with a single pulse modulator. As shown in FIG. 4A, the first pulse modulator 401 outputs the voltage HV1 or LV1 having different amplitudes to the electron gun 402, and the second pulse modulator 401 outputs the voltage HV2 or LV2 having different amplitudes to the magnetron 405, each based on a synchronization signal. Here, in the case of a grid-controlled electron gun, the first small-sized pulse modulator 401a and the second small-sized pulse modulator 4041b can supply power for the electron gun using a grid-controlled gun power supply with the grid pulse amplitude alternating, or in the case of the electron gun 402 being a bipolar electron gun, power is supplied on a time-division base by two small-sized hard tube pulse modulators (hard limiters) outputting different voltages. The pulse intervals of the pulses generated by the first and the second pulse modulators can be either the same or different from each other.

Figure 4B:
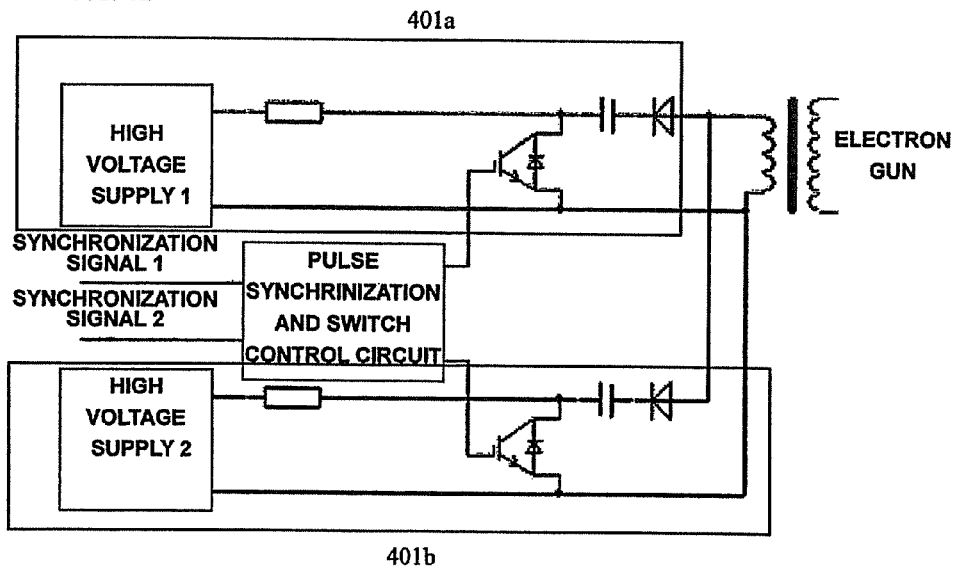
FIG. 4B is a schematic diagram showing a bipolar electron gun is supplied with power on a time-division base by two small-sized hard limiters, which constitute the pulse modulator 401 as shown in FIG. 4A and output different voltages.

FIG. 4B is a schematic diagram showing a bipolar electron gun is supplied with power on a time-division base by two small-sized hard tube pulse modulators (hard limiters), which constitute the pulse modulator 401 as shown in FIG. 4A and output different voltages. As shown in FIG. 4B, the outputs of the high-voltage power supplies 1 and 2 are connected to the driving circuit of the electron gun, which is connected to a pulse synchronization and switch control circuit. Based on the external synchronization signals 1 and 2, the pulse synchronization and switch control circuit controls the module 401a and the module 401b to output a high voltage HV1 and a relatively low voltage LV1, respectively. Given different voltage amplitudes, the electron gun 402 emits electron beams with the beam load being 10a or 11a. The second pulse modulator 404, which provides voltage for the magnetron, is similar to the first pulse modulator 401 and includes two modules (not shown) from which voltages HV2 and LV2 having different amplitudes are obtained respectively. That is, the high-voltage power supplies 1 and 2 have their outputs connected to the pulse synchronization and switch control circuit to be controlled to supply power for the magnetron on a time-division base.

The voltages HV2 and LV2 having high and low amplitudes outputted alternately from the second pulse modulator 404 cause the operating current of the magnetron 405 alternating so as to obtain microwaves having different powers alternately, such as the first microwave having the amplitude 10b and the second microwave having the amplitude 11b. In addition, as another embodiment, the magnetron 405 can be controlled such that its magnetic field intensity alternates between high and low in synchronization with its operating current pulse, in order to obtain microwaves having different powers.

Accordingly, microwaves having different powers can be fed in by two methods as follow.

1. The pulse modulator generates pulses having high and low voltage amplitudes and outputs them to the magnetron alternately so as to cause the operating current of the magnetron to alternate between high and low;

2. The magnetic field intensity of the magnetron alternates between high and low in synchronization with its operating current pulses.

By using both or either of the above methods, the alternation of the pulse power can be realized for the microwave outputted by the magnetron.

Based on the synchronization signal, the magnetron 405 feeds microwaves having different powers, such as the first or the second microwaves having microwave powers 10b or 11b, into the acceleration tube 406 by example of traveling wave or standing wave acceleration tube for accelerating the first or the second electron beam having the beam load 10a or 11a. As the synchronized acceleration approach in FIG. 2, the first or the second electron beam is accelerated inside the acceleration tube 406 to obtain accelerated electron beams having different energy levels, for example, the first and the second accelerated electron beams having energy 10c and 11c respectively. Then, the accelerated electron beams having different energy levels are used to alternately hit the efficient target 407 to generate X-ray beams having alternated high and low energy levels, such as the first and the second X-ray beams having energy 10d and 11d.

Figure 5:
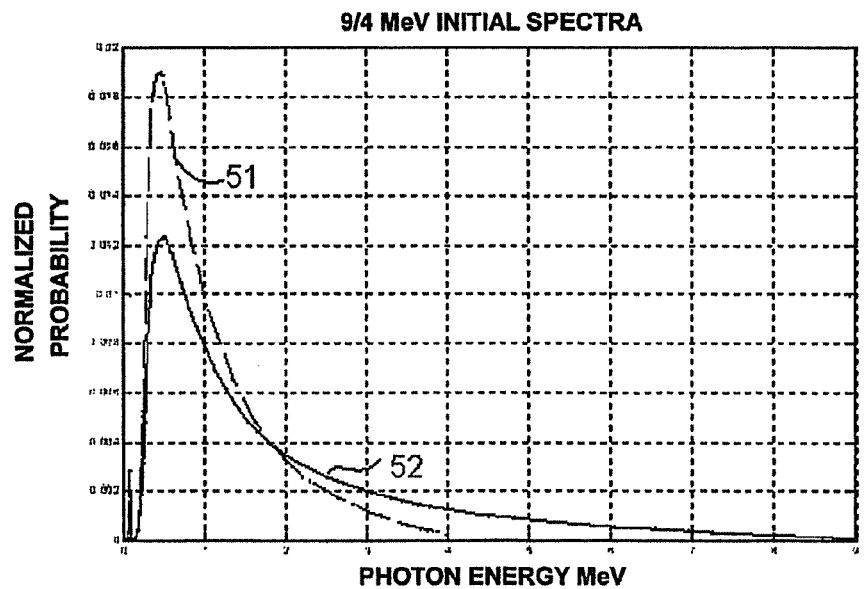
FIG. 5 is a schematic diagram of the energy spectrum difference between X-rays having two different energy levels, which are generated by the electron linac according to an embodiment of the present invention.

As a result, the accelerated electron beams having different energy levels can be obtained by changing the beam load intensity of the accelerator. Meanwhile, the energy level difference between two accelerated electron beams can be further widened by synchronously changing the microwave power fed into the acceleration tube. The X-rays, which result from the targeting by the two electron beams having different energy levels, have a large difference between energy levels. There is a great distinction between the energy spectra of the two X-ray beams. FIG. 5 shows X-ray energy spectra when the X-rays having high energy of 9 MeV and low energy of 6 MeV are outputted from the dual-energy accelerator implemented according to the present invention. Curve 51 shows the energy spectrum for low energy of 6 MeV, and Curve 52 shows the energy spectrum for high energy of 9 MeV. It can be seen in FIG. 5 that the energy levels of the two continuous spectra differ greatly from each other.

Figure 6:
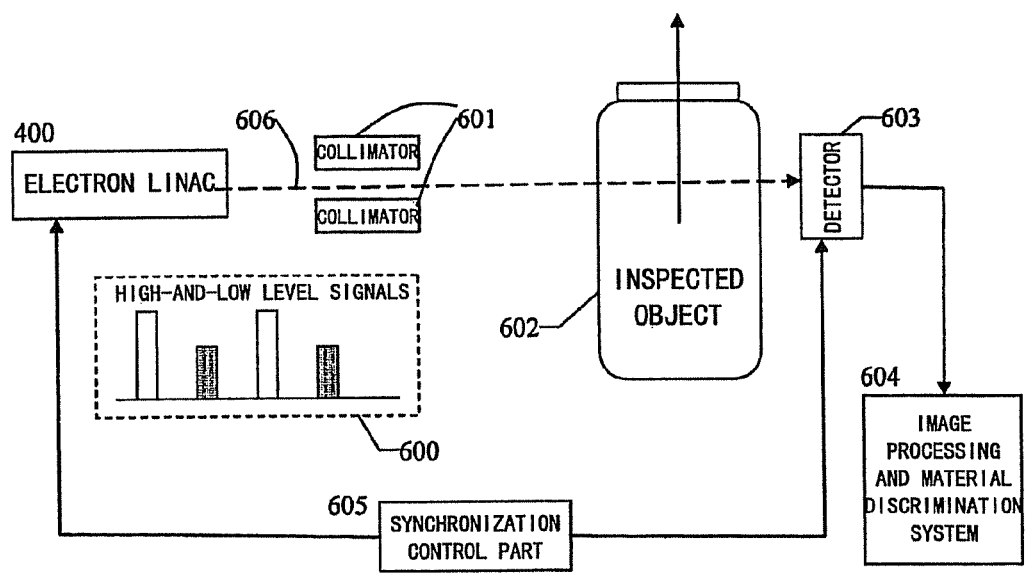
FIG. 6 is a schematic diagram of a discrimination system, which performs non-destructive inspection on container cargo and implements material discrimination by using the electron linac of the present invention.

FIG. 6 is a schematic diagram of an inspection system, which performs non-destructive inspection on container cargo and implements material discrimination by using the electron linac of the present invention. As shown in FIG. 6, the synchronization control part 605 is connected to the accelerator 400 and the detector 603 and provides them with high- and low-level signals 600 generated based on the preset parameters. Based on the synchronization signal, the accelerator 400 alternately generates X-ray beams 606 having high and low energy levels, which results in fan-shaped X-ray beams after passing through the collimator 601.

Next, the fan-shaped X-ray beams having high and low energy levels interact with the inspected object almost at the same position and then collected by the detector 603, which is connected to the image processing and material discrimination system 604 and outputs to them the digital signals. Here, the inspected object moves at certain speed in the direction shown in FIG. 6 so as to ensure the difference between the positions, at which the X-ray beams having high and low energy levels interact with the inspected object respectively, is allowable, that is, they interact at almost the same position. Therefore, the image processing and material discrimination system 604 can obtain the detection signal values D1 and D2 for high and low energy levels after the interaction with the inspected object 602 at the same position.

Then, based on the calibration curve relationship $\ln(D1/D1_0)-\ln(D2/D2_0)=f(D1)$ (where $D1_0$ and $D2_0$ are the zero load values of the high- and low-energy X-ray beams, respectively) obtained by scanning the substance of known material property, the digital signals, which are collected after the interaction between the inspected object and the dual-energy X-ray beams, are classified so as to finally determine the material property of the inspected object, such as organic matter, light metal, inorganic matter, heavy metal, etc.

The above-mentioned is only the specific embodiments of the present invention, while the scope of the present invention is not limited to it. Any modification or substitution, which is obvious to the skilled in the art within the technical range disclosed in the present invention, should be included in the scope of the present invention, which is thus defined by the claims.

What is claimed is:

1. A device for alternately generating X-rays having different energy levels comprising:
    a signal generator for generating a signal;
    a first pulse modulator connected to the signal generator for generating a first pulse voltage and a second pulse voltage;
    a second pulse modulator connected to the signal generator for generating a third pulse voltage and a fourth pulse voltage which are in synchronization with the first pulse voltage and the second pulse voltage respectively;
    a grid-controlled electron gun connected to the first pulse modulator for generating a first electron beam having a first beam load and a second electron beam having a second beam load, respectively, based on the first pulse voltage and the second pulse voltage;
    a magnetron connected to the second pulse modulator for generating a first microwave having a first power and a second microwave having a second power which is different from the first power, respectively, based on the third pulse voltage and the fourth pulse voltage;
    an acceleration tube connected to the grid-controlled electron gun for receiving the first electron beam and the second electron beam and accelerating the first electron beam and the second electron beam respectively using the first microwave and the second microwave to obtain the accelerated first electron beam and the accelerated second electron beam; and
    a target to be hit by the accelerated first electron beam and the accelerated second electron beam to generate a first X-ray and a second X-ray having different energy levels.

2. The device of claim 1, wherein the first beam load is greater than the second beam load, and the first power is smaller than the second power.

3. The device of claim 1, wherein the first beam load is smaller than the second beam load, and the first power is greater than the second power.

4. The device of claim 1, wherein the magnetron alternately change an intensity of magnetic field generated in the magnetron in synchronization with the third pulse voltage and the fourth pulse voltage to generate the first microwave and the second microwave.

5. The device of claim 1, wherein the acceleration tube is a traveling wave acceleration tube or a standing wave acceleration tube.

6. A material discrimination system comprising:
    the device of claim 1;
    a synchronization control part for generating a synchronization control signal;
    a detector for detecting X-rays after the first X-ray and second X-ray generated by the device interact with an object under inspection, based on the synchronization control signal generated by the synchronization control part, to generate digital signals; and
    an image processing and material discrimination system for classifying the digital signals for the inspected object with a predefined calibration curve to discriminate the material of the inspected object.

7. A device for alternately generating X-rays having different energy levels comprising:
    a signal generator for generating a signal;
    a pulse modulator connected to the signal generator for generating a first pulse voltage and a second pulse voltage;
    a bipolar electron gun connected to the pulse modulator for generating a first electron beam having a first beam load and a second electron beam having a second beam load, respectively, based on the first pulse voltage and second pulse voltage;

a magnetron connected to the pulse modulator for changing an intensity of magnetic field generated in the magnetron in synchronization with the first pulse voltage and second pulse voltage to generate a first microwave having a first power and a second microwave having a second power which is different from the first power;

an acceleration tube connected to the bipolar electron gun for receiving the first electron beam and the second electron beam and accelerating the first electron beam and the second electron beam respectively using the first microwave and the second microwave to obtain the accelerated first electron beam and the second electron beam; and a target to be hit by the accelerated first electron beam and accelerated second electron beam to generate a first X-ray and a second X-ray having different energy levels.

8. The device of claim 7, wherein the first beam load is greater than the second beam load, and the first power is smaller than the second power.

9. The device of claim 7, wherein the first beam load is smaller than the second beam load, and the first power is greater than the second power.

10. The device of claim 7, wherein the acceleration tube is a traveling wave acceleration tube or a standing wave acceleration tube.

11. A material discrimination system comprising:

the device of claim 7;

a synchronization control part for generating a synchronization control signal;

a detector for detecting X-rays after the first X-ray and second X-ray generated by the device interact with an object under inspection, based on the synchronization control signal generated by the synchronization control part, to generate digital signals; and an image processing and material discrimination system for classifying the digital signals for the inspected object with a predefined calibration curve to discriminate the material of the inspected object.

* * * * *